(12) United States Patent
Yokose et al.

(10) Patent No.: US 10,851,403 B2
(45) Date of Patent: Dec. 1, 2020

(54) CYCLIN-DEPENDENT KINASE SUBSTRATE

(71) Applicant: SYSMEX CORPORATION, Kobe (JP)

(72) Inventors: Noriko Yokose, Kobe (JP); Masatoshi Suganuma, Kawasaki (JP); Kenta Noda, Kobe (JP); Naoki Nishiyama, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 15/983,343

(22) Filed: May 18, 2018

(65) Prior Publication Data
US 2018/0334702 A1 Nov. 22, 2018

(30) Foreign Application Priority Data

May 19, 2017 (JP) .................................. 2017-100193

(51) Int. Cl.
- C07K 2/00 (2006.01)
- C12Q 1/48 (2006.01)
- G01N 33/50 (2006.01)
- G01N 33/68 (2006.01)
- G01N 33/573 (2006.01)
- C07K 14/00 (2006.01)

(52) U.S. Cl.
CPC .............. *C12Q 1/485* (2013.01); *C07K 2/00* (2013.01); *C07K 14/00* (2013.01); *G01N 33/5011* (2013.01); *G01N 33/573* (2013.01); *G01N 33/68* (2013.01); *C12Y 207/11022* (2013.01); *G01N 2333/916* (2013.01); *G01N 2333/91215* (2013.01); *G01N 2500/04* (2013.01)

(58) Field of Classification Search
None
See application file for complete search history.

(56) References Cited

U.S. PATENT DOCUMENTS

2012/0083427 A1* 4/2012 Klink ................... C07K 7/06
506/11

FOREIGN PATENT DOCUMENTS

| EP | 1 207 395 A1 | 5/2002 |
| WO | 0140264 A3 | 6/2001 |
| WO | 2005012329 A2 | 2/2005 |

OTHER PUBLICATIONS

Holmes et al., "A Predictive Scale for Evaluating Cyclin-dependent Kinase Substrates: A Comparison of p34cdc2 and p33cdk2," J. Biol. Chem. 271: 25240-25246 (1996) (Year: 1996).*
UniProtKB Accession No. A0A081EU07, accessed Oct. 25, 2019 at URL uniprot.org/uniprot/A0A081EU07, 4 pages (Year: 2019).*
Catalano, A., et al., "Synthesis and biological activity of peptides equivalent to the IP22 repeat motif found in proteins *Dictyostelium* and Mimivirus", Peptides, vol. 31, No. 10, 2010, pp. 1799-1805.
Kitagawa, M., et al., "The consensus motif for phosphorylation by cyclin D1-Cdk4 Is different from that for phosphorylation by cyclin A/E-Cdk2", The EMBO Journal, vol. 15, No. 24, 1996, pp. 7060-7069, XP-001122365.
The Communication pursuant to Article 94(3) EPC dated Jul. 7, 2020 in a counterpart European patent application No. 18173066.4.

* cited by examiner

*Primary Examiner* — Julie Ha
*Assistant Examiner* — Kristina M Hellman
(74) *Attorney, Agent, or Firm* — Sughrue Mion, PLLC

(57) ABSTRACT

Disclosed is a cyclin-dependent kinase substrate including a polypeptide that contains an amino acid sequence represented by formula (1): $R^1$—P (wherein $R^1$ represents a serine residue or a threonine residue, P represents a proline residue, "—" represents a single bond, and the left side represents the N-terminal side), and satisfies the following (a1) and/or (b1): (a1) the second amino acid residue counting from the proline residue toward the N-terminal side in the formula (1) is an aromatic amino acid residue, and/or (b1) at least two amino acid residues from the proline residue toward the C-terminal side in the formula (1) are acidic amino acid residues.

5 Claims, 2 Drawing Sheets

Specification includes a Sequence Listing.

CYCLIN-DEPENDENT KINASE SUBSTRATE

CROSS REFERENCE TO RELATED APPLICATIONS

This application claims priority from prior Japanese Patent Application No. 2017-100193, filed on May 19, 2017, entitled "CYCLIN-DEPENDENT KINASE SUBSTRATE", the entire contents of which are incorporated herein by reference.

TECHNICAL FIELD

The present invention relates to a cyclin-dependent kinase substrate.

BACKGROUND

Various physiological responses, diseases such as cancer and the like are deeply involved in the regulatory mechanism of multiple continuous reactions (cell cycle) including cell growth, DNA replication, chromosome distribution, cell division, and the like. This cell cycle is regulated by the activity of cyclin-dependent kinase that is mainly a phosphorylated enzyme.

The activity of cyclin-dependent kinase is usually activated by the binding of cyclins and is inactivated by the binding of cyclin-dependent kinase inhibitors. Further, it has been reported that there are plural kinds of cyclin-dependent kinases, and representatively cyclin-dependent kinases 1, 2, 4, 6, and the like exist. They usually control different reactions in the cell cycle, respectively.

Therefore, it is important to construct a system to evaluate the activity of cyclin-dependent kinase to analyze various physiological responses, diseases, and the like.

For example, cyclin-dependent kinases 4 and 6 are regarded as molecular targets for breast cancer. From this fact, the present inventor has focused on evaluating the activity of these cyclin-dependent kinases.

EP 1 207 395 A1 has reported a method for evaluating the activity of cyclin-dependent kinase 4 or 6, by detecting phosphorylation using specific antibodies against different phosphorylation sites for each kinase, using RB (retinoblastoma) protein as a substrate. However, since the RB protein has a relatively large molecular weight, it is considered to be difficult to form into a reagent, from the viewpoints of production cost, stability, and the like.

On the other hand, for a substrate peptide with a relatively small molecular weight, it is generally known that the optimal consensus sequence of the phosphorylation target site of the cyclin-dependent kinase is (S/T) PX (K/R) (X is an arbitrary amino acid residue). However, commercially available cyclin-dependent kinase 4/6 substrate peptides containing this consensus sequence have low reactivity and low specificity.

As a result of intensive studies in view of the above problems, the present inventor has found that the above object can be solved by a polypeptide satisfying that the second amino acid residue counting from the proline residue toward the N-terminal side in the phosphorylation site (SP or TP) of the cyclin-dependent kinase is an aromatic amino acid residue and/or at least two amino acid residues from the proline residue toward the C-terminal side are acidic amino acid residues. As a result of advancing further research based on this finding, the present inventor has completed the present invention.

SUMMARY OF THE INVENTION

The scope of the present invention is defined solely by the appended claims, and is not affected to any degree by the statements within this summary.

More specifically, the present invention includes the following embodiments as an embodiment:

a first aspect of the present invention is a cyclin-dependent kinase substrate including a polypeptide that contains an amino acid sequence represented by formula (1): $R^1$—P (wherein $R^1$ represents a serine residue or a threonine residue, P represents a proline residue, "—" represents a single bond, and the left side represents the N-terminal side), and satisfies (a1) and/or (b1) below: (a1) the second amino acid residue counting from the proline residue toward the N-terminal side in the formula (1) is an aromatic amino acid residue, and/or (b1) at least two amino acid residues from the proline residue toward the C-terminal side in the formula (1) are acidic amino acid residues.

DETAILED DESCRIPTION OF THE PREFERRED EMBODIMENTS

In the present specification, the expressions "containing" and "including" include the concepts of "containing", "including", "consisting essentially of" and "consisting only of".

As used herein, amino acids include both natural amino acids and artificial amino acids.

As used herein, the "residue" of various amino acids is a constituent unit of amino acids constituting a polypeptide, and represents a group in which hydrogen atoms are excluded from the amino group in the main chain and/or —OH is excluded from the carboxyl group in the main chain, from the amino acids.

Figure 1:
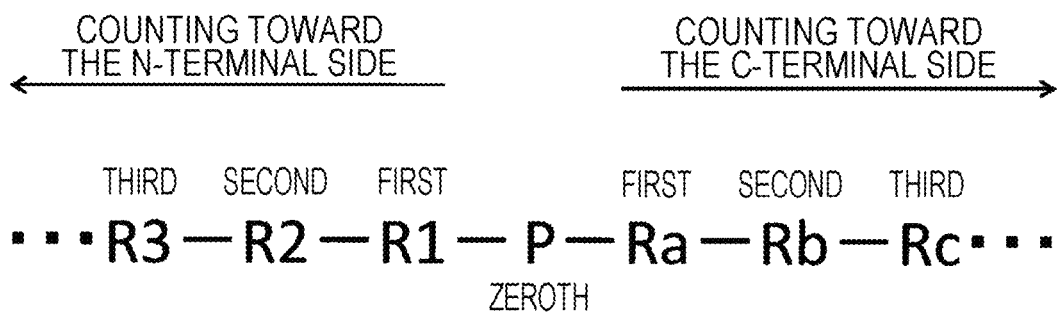
FIG. 1 is a schematic view showing an amino acid residue represented by the expression "Nth amino acid residue counting from the proline residue toward the N-terminal (or C-terminal) side in the formula (1)", as used herein.

As used herein, the "Nth amino acid residue counting from the proline residue toward the N-terminal (or C-terminal) side in the formula (1)" means, in the polypeptide including an amino acid sequence containing the amino acid sequence of the formula (1), an Nth amino acid residue counting toward the N-terminal (or C-terminal) side, using the proline residue in the formula (1) as the base point (the 0th amino acid), as exemplified in FIG. 1. The same applies to amino acid residues represented by the same expression.

As used herein, the "reactivity" between cyclin-dependent kinase and a substrate can be measured with the degree of modification of a substrate by cyclin-dependent kinase as an index. The degree of modification of a substrate by cyclin-dependent kinase can be measured, for example, as in Test Example 1 or the like.

As used herein, the combination of cyclin-dependent kinase and cyclin is not particularly limited.

1. Cyclin-Dependent Kinase Substrate

The present disclosure relates to, in an embodiment thereof, a cyclin-dependent kinase substrate (sometimes also referred to herein as "the substrate of the present disclosure") including a polypeptide that contains an amino acid sequence represented by formula (1): $R^1$—P (wherein $R^1$ represents a serine residue or a threonine residue, P represents a proline residue, "—" represents a single bond, and the left side represents the N-terminal side), and satisfies the following (a1) and/or (b1):

(a1) the second amino acid residue counting from the proline residue toward the N-terminal side in the formula (1) is an aromatic amino acid residue, and/or (b1) at least two amino acid residues from the proline residue toward the C-terminal side in the formula (1) are acidic amino acid residues. This will be described below.

The amino acid sequence represented by the formula (1): $R^1$-P is an amino acid sequence containing the amino acid residue ($R^1$) to be phosphorylated by cyclin-dependent kinase. $R^1$ is preferably a serine residue.

From the viewpoint of further improving the reactivity to cyclin-dependent kinase (in particular, at least one selected from the group consisting of cyclin-dependent kinase 4 and cyclin-dependent kinase 6), the substrate of the present disclosure preferably satisfies requirement (a1), that is, the second amino acid residue counting from the proline residue toward the N-terminal side in the formula (1) is an aromatic amino acid residue.

The aromatic amino acid residue in the requirement (a1) is not particularly limited as long as it is an amino acid residue having an aromatic group on the side chain (preferably, the terminal of the side chain is an aromatic group). The aromatic group is not particularly limited as long as it does not significantly inhibit the phosphorylation reaction of the substrate of the present disclosure by cyclin-dependent kinase. Examples of the aromatic group include aryl groups having a ring-constituting carbon atom number of 6 to 20, preferably 6 to 12 and further preferably 6 to 8, specifically, monocyclic or polycyclic aryl groups such as a phenyl group, a hydroxyphenyl group, a naphthyl group, a biphenyl group, a pentalenyl group, an indenyl group, an anthranyl group, a tetracenyl group, a pentacenyl group, a pyrenyl group, a perylenyl group, a fluorenyl group and a phenanthryl group, heteroaryl groups having a ring-constituting atom number of 3 to 20, preferably 3 to 12 and more preferably 7 to 11 (preferably, a heteroaryl group wherein the hetero atom is a nitrogen atom), specifically, monocyclic or polycyclic heteroaryl groups such as a pyrrolyl group, a pyridyl group, a pyrrolidyl group, a piperidyl group, an imidazolyl group, a pyrazolyl group, a pyrazyl group, a pyrimidyl group, a pyridazyl group, a piperazyl group, a triazinyl group, an oxazolyl group, an isoxazolyl group, a morpholyl group, a thiazolyl group, an isothiazolyl group, a furanyl group, a thiophenyl group, an indolyl group, a quinolyl group, an isoquinolyl group, a benzimidazolyl group, a quinazolyl group, a phthalazyl group, a purinyl group, a pteridyl group, a benzofuranyl group, a coumaryl group, a chromonyl group and a benzothiophenyl group, and the like.

From the viewpoint of further improving the reactivity to cyclin-dependent kinase (in particular, at least one selected from the group consisting of cyclin-dependent kinase 4 and cyclin-dependent kinase 6), examples of the aromatic group include preferably heteroaryl groups, more preferably heteroaryl groups in which the hetero atom is a nitrogen atom, further preferably heteroaryl groups in which the hetero atom is 1 to 3 nitrogen atom(s) (preferably 1), and furthermore preferably heteroaryl groups having a ring-constituting atom number of 7 to 11 in which the hetero atom is one nitrogen atom, and particularly preferably an indolyl group.

A preferred embodiment of the aromatic amino acid residue includes an amino acid residue in which the side chain is represented by formula (A): —$L^A$—$R^A$ (wherein $L^A$ represents an optionally substituted alkylene group, $R^A$ represents an aromatic group, and "—" represents a single bond).

The alkylene group represented by $L^A$ is not particularly limited, and examples thereof include linear or branched (preferably linear) alkylene groups having a carbon atom number of 1 to 6, preferably 1 to 4, more preferably 1 to 2, and further preferably 1. Examples of the alkylene group include a methylene group, an ethylene group, a propylene group, a butylene group, a pentylene group, a hexylene group, and the like.

The alkylene group represented by $L^A$ is optionally substituted. The substituent is not particularly limited as long as it does not significantly inhibit the phosphorylation reaction of the substrate of the present disclosure by cyclin-dependent kinase, and examples thereof include an amino group, a carboxyl group, a carbamoyl group, a hydroxyl group, and the like. The number of substituents is not particularly limited, and is, for example, 0 to 3, preferably 0 to 1, and more preferably 0.

The aromatic group represented by $R^A$ is the same as the aromatic group described above.

Specific examples of the aromatic amino acid residue include a tryptophan residue, a phenylalanine residue, a tyrosine residue, a histidine residue, a thyroxine residue, and the like, preferably a tryptophan residue, a phenylalanine residue, a tyrosine residue, and the like, and more preferably a tryptophan residue.

From the viewpoint of further improving the specificity to at least one selected from the group consisting of cyclin-dependent kinase 4 and cyclin-dependent kinase 6, the substrate of the present disclosure preferably satisfies requirement (b1), that is, at least two (preferably 2 to 5, more preferably 2 to 4, and further preferably 2 to 3) amino acid residues from the proline residue toward the C-terminal side in the formula (1) are acidic amino acid residues.

The phrase "at least two amino acid residues from the proline residue toward the C-terminal side in the formula (1)" means, in other words, at least two amino acid residues of the first to nth (n is an arbitrary integer) amino acid residues counting from the proline residue toward the C-terminal side in the formula (1).

The acidic amino acid residue in the requirement (b1) is not particularly limited as long as it is an amino acid residue having an acidic side chain (for example, having an acidic group on the side chain, and preferably, the terminal of the side chain is an acidic group). The acidic group is not particularly limited as long as it does not significantly inhibit the phosphorylation of the substrate of the present disclosure by cyclin-dependent kinase. Examples of the acidic group include a carboxyl group, a sulfonate group, a phosphate group, a sulfate group, a hydroxyphenyl group, and the like, and preferably a carboxyl group. The number of acidic groups on the side chain of the acidic amino acid residue is not particularly limited, and is, for example, 1 to 4, preferably 1 to 3, more preferably 1 to 2, and further preferably 2.

A preferred embodiment of the acidic amino acid residue includes amino acid residues in which the side chain is represented by formula (B): —$L^B$—$R^B$ (wherein $L^B$ represents an optionally substituted alkylene group, $R^B$ represents an acidic group, and "—" represents a single bond).

The alkylene group represented by $L^B$ is not particularly limited, and examples thereof include linear or branched (preferably linear) alkylene groups having a carbon atom number of 1 to 6, preferably 1 to 4, more preferably 1 to 3, further preferably 1 to 2, and further more preferably 2. Examples of the alkylene group include a methylene group, an ethylene group, a propylene group, a butylene group, a pentylene group, a hexylene group, and the like.

The alkylene group represented by $L^B$ is optionally substituted. The substituent is not particularly limited as long as it does not significantly inhibit the phosphorylation reaction of the substrate of the present disclosure by cyclin-dependent kinase and does not greatly impair the degree of acidity of the acidic side chain. Examples thereof include the acidic groups described above, a carbamoyl group, a hydroxyl group, and the like, and preferably the acidic groups described above. The number of substituents is not particularly limited, and is, for example, 0 to 3, preferably 1 to 2, and more preferably 1.

The acidic group represented by $R^B$ is the same as the acidic group described above.

The acidic amino acid residue is preferably a residue of an amino acid having an isoelectric point of 4 or less, and more preferably 2 to 4.

Specific examples of the acidic amino acid residues include an aspartic acid residue, a glutamic acid residue, amino acid residues in which an alkylene group on the side chain of an aspartic acid residue or a glutamic acid residue is substituted with, for example, 1 to 3, preferably 1 to 2, and more preferably 1 acidic group (preferably a carboxy group), and the like.

From the viewpoint of further improving the reactivity to cyclin-dependent kinase (in particular, at least one selected from the group consisting of cyclin-dependent kinase 4 and cyclin-dependent kinase 6), the substrate of the present disclosure preferably further satisfies at least one requirement selected from the group consisting of the requirements (a2), (a3), (a4), (a5), (a6), (a7), (a8), (a9) and (a10):

(a2) the fifth amino acid residue counting from the proline residue toward the C-terminal side in the formula (1) is a basic amino acid residue, (a3) the third amino acid residue counting from the proline residue toward the N-terminal side in the formula (1) is a ring structure-containing amino acid residue, (a4) the sixth amino acid residue counting from the proline residue toward the C-terminal side in the formula (1) is a glycine residue, (a5) either of (a5A) the fourth amino acid residue counting from the proline residue toward the N-terminal side in the formula (1) is an alanine residue, and (a5B) the fourth amino acid residue counting from the proline residue toward the N-terminal side in the formula (1) is a methionine residue, (a6) the second amino acid residue counting from the proline residue toward the C-terminal side in the formula (1) is a proline residue, (a7) the third amino acid residue counting from the proline residue toward the C-terminal side in the formula (1) is a tryptophan residue, (a8) the first amino acid residue counting from the proline residue toward the C-terminal side in the formula (1) is an asparagine residue, (a9) the fourth amino acid residue counting from the proline residue toward the C-terminal side in the formula (1) is a tryptophan residue, and (a10) the fifth amino acid residue counting from the proline residue toward the N-terminal side in the formula (1) is a glycine residue, in addition to the requirement (a1) and/or (b1).

In the requirement (a2), the basic amino acid residue is not particularly limited as long as it is an amino acid residue having a basic side chain. The basic side chain is not particularly limited, and examples thereof include a side chain having an amino group, a group obtained by removing one hydrogen atom from an aromatic ring which is an amine, and the like. The basic amino acid residue is, for example, a residue of an amino acid having an isoelectric point of greater than 7, and preferably an amino acid residue having an isoelectric point of 7.5 or more. Specific examples of the basic amino acid residue include an arginine residue, a lysine residue, a histidine residue, and the like, and preferably an arginine residue.

The ring structure-containing amino acid residue in the requirement (a3) is an amino acid residue containing a cyclic amino acid residue such as proline, in addition to the aromatic amino acid residue in the requirement (a1). The ring structure-containing amino acid residue in the requirement (a3) is preferably a cyclic amino acid residue, and more preferably a proline residue.

The combination of the requirements (a2), (a3), (a4), (a5), (a6), (a7), (a8), (a9) and (a10) is arbitrary. In a preferred embodiment of the substrate of the present disclosure, the substrate satisfies the requirements including five requirements of the requirements (a3), (a4), (a5) (preferably (a5A)), (a7) and (a10). In a more preferred embodiment, the substrate satisfies the requirements including six requirements of the requirements (a3), (a4), (a5) (preferably (a5A)), (a6), (a7) and (a10).

From the viewpoint of further improving the reactivity to cyclin-dependent kinase (in particular, at least one selected from the group consisting of cyclin-dependent kinase 4 and cyclin-dependent kinase 6), it is more preferable that at least one requirement selected from the group consisting of the requirements (a2), (a3), (a4), (a5), (a6), (a7) and (a8) is satisfied, it is more preferable that at least one requirement selected from the group consisting of the requirements (a2), (a3), (a4) and (a5) is satisfied, and it is further preferable that at least one requirement selected from the group consisting of the requirements (a2), (a3), (a4) and (a5A) is satisfied.

From the viewpoint of further improving the specificity to at least one selected from the group consisting of cyclin-dependent kinase 4 and cyclin-dependent kinase 6, the substrate of the present disclosure preferably further satisfies at least one requirement selected from the group consisting of requirements (b2), (b3), (b4) and (b5):

(b2) at least one amino acid residue of the first to third amino acid residues counting from the proline residue toward the C-terminal side in the formula (1) is an acidic amino acid residue, (b3) at least two amino acid residues of the first to tenth amino acid residues counting from the proline residue toward the C-terminal side in the formula (1) are acidic amino acid residues, (b4) the first amino acid residue counting from the proline residue toward the C-terminal side in the formula (1) is not a basic amino acid residue, and (b5) all amino acid residues of the first to fifth amino acid residues counting from the proline residue toward the C-terminal side in the formula (1) are not basic amino acid residues, in addition to the requirements (a1) and/or (b1).

The combination of the requirements (b2), (b3), (b4) and (b5) is arbitrary. In a preferred embodiment of the substrate of the present disclosure, the requirements including the requirements (b2) and (b3) are satisfied, in a more preferred embodiment, the requirements including the requirements (b2), (b3) and (b4) are satisfied, and in a further preferred embodiment, all of (b2), (b3), (b4) and (b5) are satisfied.

The acidic amino acid residues in the requirements (b2), (b3), (b4) and (b5) are the same as the acidic amino acid residue in the requirement (b1).

In the requirement (b2), one that is the acidic amino acid residue is preferably at least one amino acid residue of the first to second counting from the proline residue toward the C-terminal side in the formula (1). In addition, in the requirement (b2), the number of acidic amino acid residues is preferably 1 to 3, more preferably 1 to 2, and further preferably 1.

In the requirement (b3), those that are the acidic amino acid residues are preferably at least two amino acid residues of the first to eighth (preferably first to seventh, more preferably first to sixth) amino acid residues counting from the proline residue toward the C-terminal side in the formula (1). In addition, in the requirement (b3), the number of acidic amino acid residues is, for example, 2 to 7, preferably 2 to 5, more preferably 2 to 4, and further preferably 2 to 3.

In the requirements (b4) and (b5), the basic amino acid residue is not particularly limited as long as it is an amino acid residue having a basic side chain. The basic side chain is not particularly limited, and examples thereof include a side chain having an amino group, a group obtained by removing one hydrogen atom from an aromatic ring which is an amine, and the like. The basic amino acid residue is, for example, a residue of an amino acid having an isoelectric point of greater than 7, and preferably an amino acid residue having an isoelectric point of 7.5 or more. Specific examples of the basic amino acid residue include a histidine residue, a lysine residue, an arginine residue, and the like.

Examples of the amino acid residue that "is not a basic amino acid" in the requirements (b4) and (b5) include amino acid residues having an acidic side chain such as aspartic acid or glutamic acid; amino acid residues having an antistatic polar side chain such as glycine, asparagine, glutamine, serine, threonine, tyrosine or cysteine; amino acid residues having a nonpolar side chain such as alanine, valine, leucine, isoleucine, proline, phenylalanine, methionine or tryptophan; amino acid residues having a β-branched side chain such as threonine, valine or isoleucine; amino acid residues having an aromatic side chain such as tyrosine, phenylalanine or tryptophan; and the like.

The number of amino acid residues constituting the polypeptide as the substrate of the present disclosure is not particularly limited, and is, for example, 50 or less, preferably 4 to 40, more preferably 6 to 30, and further preferably 7 to 20. In a preferred embodiment of the polypeptide as the substrate of the present disclosure, at least three amino acid residues are present on the N-terminal side of the amino acid sequence represented by the formula (1), and/or at least two amino acid residues are present on the C-terminal side of the amino acid sequence represented by the formula (1).

Examples of the polypeptide as the substrate of the present disclosure also include those to which various tags (for example, a biotin tag, a His tag, a FLAG tag, a Halo tag, a MBP tag, a HA tag, a Myc tag, a V5 tag, a PA tag, and the like) are attached via an appropriate linker as necessary, as long as the phosphorylation reaction of the substrate of the present disclosure by cyclin-dependent kinase is not significantly inhibited.

Examples of the polypeptide as the substrate of the present disclosure also include those in which terminal amino acid residues are chemically modified as long as the phosphorylation reaction of the substrate of the present disclosure by cyclin-dependent kinase is not significantly inhibited.

Examples of the polypeptide as the substrate of the present disclosure also include those in which the C terminus is a carboxyl group (—COOH), a carboxylate (—COO$^-$), an amide (—CONH$_2$) or an ester (—COOR), and the like.

As R in the ester, for example, a $C_{1-6}$ alkyl group such as methyl, ethyl, n-propyl, isopropyl or n-butyl; a $C_{3-8}$ cycloalkyl group such as cyclopentyl or cyclohexyl; for example, a $C_{6-12}$ aryl group such as phenyl or α-naphthyl; for example, a phenyl-$C_{1-2}$ alkyl group such as benzyl or phenethyl; a $C_{7-14}$ aralkyl group such as α-naphthyl-$C_{1-2}$ alkyl group such as α-naphthylmethyl; a pivaloyloxymethyl group or the like is used.

Examples of the polypeptide as the substrate of the present disclosure also include a polypeptide in which the amino group of the N-terminal amino acid residue is protected with a protecting group (for example, a $C_{1-6}$ acyl group such as $C_{1-6}$ alkanoyl such as a formyl group or an acetyl group), and the like.

Examples of the polypeptide as the substrate of the present disclosure also include those in which the amino acid residue other than the amino acid residues constituting the formula (1), the requirements (a1), and (b1) to (b4) (preferably, amino acid residues constituting the formula (1), the requirements (a1) to (a5), and (b1) to (b4), more preferably, amino acid residues constituting the formula (1), the requirements (a1) to (a8), and (b1) to (b4), further preferably, amino acid residues constituting the formula (1), the requirements (a1) to (a10), and (b1) to (b4)) are chemically modified, as long as the phosphorylation reaction of the substrate of the present disclosure by cyclin-dependent kinase is not significantly inhibited. Examples of the chemical modification in this case include amidation and esterification of a carboxyl group; protection of an amino group by a protecting group; and the like. The esterification and the protecting group are the same as the above-described terminal chemical modification.

Examples of the polypeptide as the substrate of the present disclosure also include a salt form with an acid or a base. The salt is not particularly limited, and any of an acidic salt and a basic salt can be adopted. Examples of the acidic salt include inorganic acid salts such as hydrochlorides, hydrobromides, sulfates, nitrates and phosphates; organic acid salts such as acetates, propionates, tartrates, fumarates, maleates, malates, citrates, methanesulfonates and paratoluenesulfonates; amino acid salts such as aspartates and glutamates; and the like. Examples of the basic salt include alkali metal salts such as sodium salts and potassium salts; alkaline earth metal salts such as calcium salts and magnesium salts; and the like.

Examples of the polypeptide as the substrate of the present disclosure also include solvate forms. The solvent is not particularly limited, and examples thereof include water, ethanol, glycerol, acetic acid, and the like.

In a preferred embodiment, the substrate of the present disclosure shows specific reactivity to at least one selected from the group consisting of cyclin-dependent kinase 4 and cyclin-dependent kinase 6. For example, the substrate of the present disclosure has a reactivity value for at least one selected from the group consisting of cyclin-dependent kinase 4 and cyclin-dependent kinase 6 that is, for example, 1.5 times, preferably 2 times, more preferably 5 times, further preferably 10 times, further more preferably 20 times, and particularly preferably 50 times, as the average value of the reactivity value for cyclin-dependent kinase 1 and the reactivity value for cyclin-dependent kinase 2. As another example, the substrate of the present disclosure has a reactivity value for cyclin-dependent kinase 6 that is, for example, 1.5 times, preferably 2 times, more preferably 5 times, further preferably 10 times, further more preferably 20 times, and particularly preferably 50 times, as the average value of the reactivity value for cyclin-dependent kinase 1, the reactivity value for cyclin-dependent kinase 2, and the reactivity value for cyclin-dependent kinase 4.

Thus, in a preferred embodiment, the substrate of the present disclosure is particularly useful as at least one substrate selected from the group consisting of cyclin-dependent kinase 4 and cyclin-dependent kinase 6, or as a substrate for cyclin-dependent kinase 6.

2. Method for Measuring Cyclin-Dependent Kinase Activity

In an embodiment thereof, the present disclosure relates to a method for measuring the cyclin-dependent kinase activity of a test sample (sometimes also referred to herein as "the measurement method of the present disclosure"), including the following steps (i) and (ii): (i) bringing the test sample into contact with the substrate of the present disclosure, and (ii) measuring the amount of a substance produced by cyclin-dependent kinase in the test sample. This will be described below.

The measurement method of the present disclosure is a method in which all steps are performed in vitro.

The test sample is not particularly limited as long as it is a sample that can contain cyclin-dependent kinase. As the test sample, for example, an extract of a cell sample or a tissue sample collected from an organism (hereinafter collectively referred to as "biological sample") or a purified product thereof can be adopted.

The organism from which the biological sample is derived is not particularly limited as long as it is an organism that can contain cyclin-dependent kinase, and examples thereof include various mammals such as human, monkey, mouse, rat, dog, cat, and rabbit. Among them, human is preferred.

Examples of the cell sample include blood cells, hematopoietic stem cells/progenitor cells, gametes (sperm, ovum), fibroblasts, epithelial cells, vascular endothelial cells, neuronal cells, hepatocytes, keratinocytes, myocytes, epidermal cells, endocrine cells, ES cells, iPS cells, tissue stem cells, cancer cells (for example, kidney cancer cells, leukemia cells, esophageal cancer cells, gastric cancer cells, colon cancer cells, liver cancer cells, pancreatic cancer cells, lung cancer cells, prostate cancer cells, skin cancer cells, breast cancer cells, cervical cancer cells, and the like), and the like, and preferably breast cancer cells.

The tissue sample is not particularly limited, and examples thereof include samples of epithelial tissue, connective tissue, muscle tissue, nerve tissue, and the like.

The biological sample contains, for example, blood cells, hematopoietic stem cells/progenitor cells, gametes (sperm, ovum), fibroblasts, epithelial cells, vascular endothelial cells, neuronal cells, hepatocytes, keratinocytes, myocytes, epidermal cells, endocrine cells, ES cells, iPS cells, tissue stem cells, cancer cells (for example, kidney cancer cells, leukemia cells, esophageal cancer cells, gastric cancer cells, colon cancer cells, liver cancer cells, pancreatic cancer cells, lung cancer cells, prostate cancer cells, skin cancer cells, breast cancer cells, cervical cancer cells, and the like), and the like. Examples of the biological sample preferably include biological samples containing breast cancer cells.

The extract of the biological sample is not particularly limited as long as it is a cell membrane or nuclear membrane disruptive product in the biological sample. Disruption of cell membranes or nuclear membranes is obtained by subjecting the biological sample to solubilization treatment. The solubilization treatment can be performed by subjecting the biological sample to ultrasonic treatment in a buffer solution for solubilization treatment (hereinafter referred to as "solubilizing agent"), suction stirring with a pipette, or the like.

The solubilizing agent is a buffer solution containing a substance that disrupts cell membranes or nuclear membranes. The solubilizing agent may further contain a substance that inhibits denaturation or degradation of cyclin-dependent kinase or the like.

Examples of the substance that disrupts cell membranes or nuclear membranes include, but are not particularly limited to, surfactants, chaotropic agents, and the like. The surfactant can be used within the range not inhibiting the activity of the kinase to be measured. Examples of the surfactant include polyoxyethylene alkylphenyl ethers such as Nonidet P-40 (NP-40), Triton X-100 (registered trademark of Dow Chemical Company), deoxycholic acid, CHAPS, and the like. The substance that disrupts cell membranes or nuclear membranes may be used alone or in combination of two or more kinds. The concentration of the substance that disrupts cell membranes or nuclear membranes in the solubilizing agent is usually 0.1 to 2 w/v %.

Examples of the substance that inhibits denaturation or degradation of cyclin-dependent kinase include, but are not particularly limited to, protease inhibitors, and the like. Examples of the protease inhibitor include, but are not particularly limited to, metalloprotease inhibitors such as EDTA and EGTA; serine protease inhibitors such as PMSF, trypsin inhibitor and chymotrypsin; cysteine protease inhibitors such as iodoacetamide and E-64; and the like. These substances that inhibits denaturation or degradation of kinase may be used alone or in combination of two or more. The concentration of the substance that inhibits denaturation or degradation of kinase in the solubilizing agent is usually 0.5 to 10 mM, in the case of EDTA, EGTA and PMSF.

Purification of the extract of the biological sample can be performed according to or pursuant to known methods. Examples thereof include removal of insoluble matter, concentration of cyclin-dependent kinase, and the like. The method for concentrating cyclin-dependent kinase is not particularly limited, and examples thereof include an immunoprecipitation method using an antibody against cyclin-dependent kinase, and the like.

Contact between the test sample and the substrate of the present disclosure is not particularly limited as long as the cyclin-dependent kinase is under the condition that the substrate of the present disclosure can be modified by its enzymatic action. The contact is usually performed in a buffer solution, in the presence of a modifying group donor such ATP, an ATP labeled substance or an ATP derivative.

As the buffer solution, a buffer solution capable of maintaining a pH (usually 6 to 8, preferably 7 to 7.8) capable of exerting the activity of cyclin-dependent kinase is preferably used, for example, a HEPES buffer solution, a Tris hydrochloride buffer solution or the like is used. The buffer solution contains a metal ion necessary for exerting the activity of cyclin-dependent kinase, for example, a magnesium ion, a manganese ion or the like, as necessary.

The ATP labeled substance is not particularly limited, and examples thereof include a radioisotope ATP labeled substance obtained by replacing the phosphorus atom constituting ATP with a radioactive isotope (for example, $^{32}P$).

The ATP derivative is not particularly limited, and examples thereof include ATP-γS (adenosine-5'-(γ-thio)-triphosphate) disclosed in JP 2002-335997 A, a DNP group-linked ATP derivative in which a dinitrophenyl (DNP) group is linked to the γ position of ATP disclosed in JP 2015-192635 A, and the like.

By the above contact, the amino acid residue represented by $R^1$ in the formula (1) of the substrate of the present disclosure is modified by the enzymatic action of cyclin-dependent kinase, depending on the activity of cyclin-dependent kinase of the test sample. The modification mode varies depending on the conditions of contact and the modifying group donor. For example, when using ATP as a modifying group donor, modification is addition of a phosphate group, and when using a radioactive isotope ATP labeled substance as a modifying group donor, modification is addition of a radioisotope-labeled phosphate group, when using ATP-γS as a modifying group donor, modification is addition of a thiophosphate group, and when using a DNP group-linked ATP derivative is used as a modifying group donor, it is addition of a DNP group-linked phosphate group.

In the measurement method of the present disclosure, cyclin-dependent kinase activity can be measured by measuring the amount of a substance produced, by cyclin-dependent kinase in the test sample by the contact between the test sample and the substrate of the present disclosure. In other words, the quantitative value of the amount of the substance can be regarded as the cyclin-dependent kinase activity value. Examples of the substance include modified substrates (=modified substances) of the present disclosure, and substances derived from a modifying group (for example, a phosphate group, a radioisotope-labeled phosphate group, a thiophosphate group, a DNP group-linked phosphate group, or the like) donor (for example, ADP or the like), and preferably modified substrates of the present disclosure.

The amount of the produced substance can be measured according to or pursuant to known methods, depending on the type of the substance, the modification mode, and the like. For the measurement, for example, a reaction with a specific binding partner (may be added with a labeling substance) to a peptide to which a phosphate group, a DNP group-linked phosphate group or the like is added; a reaction with a labeling substance having a binding site to a thiophosphate group (for example, alkyl halide, maleimide, an aziridine moiety or the like), a reaction with a specific binding partner (may be added with a labeling substance) to various labeling substances, luminescence reaction/detection based on enzymatic action, fluorescence detection, radiation detection, chromatography, mass spectrometry, electrophoresis, and the like can be performed singly or in appropriate combination.

Examples of the specific binding partners include antibodies. Examples of the labeling substance include fluorescent substances, enzymes, biotin, and the like. Examples of the fluorescent substance include, but are not particularly limited to, fluorescein derivatives such as iodoacetyl-fluorescein isothiocyanate, 5-(bromomethyl)fluorescein, fluorescein-5-maleimide, 5-iodoacetamidofluorescein and 6-iodoacetamidofluorescein; coumarin derivatives such as 4-bromomethyl-7-methoxycoumarin; eosin derivatives such as eosin 5-maleimide and eosin-5-iodoacetamide; phenanthroline derivatives such as N-(1,10-phenanthrolin-5-yl)bromoacetamide; pyrene derivatives such as 1-pyrenebutyryl chloride, N-(1-pyreneethyl)iodoacetamide, N-(1-pyrenemethyl)iodoacetamide and 1-pyrenemethyliodoacetate; rhodamine derivatives such as Rhodamine Red C2 Maleimide; and the like. Examples of the enzyme include, but are not particularly limited to, β-galactosidase, alkaline phosphatase, glucose oxidase, peroxidase, and the like.

When the produced substance is the modified substrate, in a preferred embodiment of the measurement method of the present disclosure, the step (ii) includes the following steps (iia) and (iic): (iia) mixing the modified substrate with a binding molecule for the modified substrate to form a complex containing the modified substrate and the binding molecule, and (iic) measuring the amount of the modified substrate by measuring the amount of the complex.

The binding molecule is not particularly limited as long as it is a molecule capable of specifically binding to the modified substrate and can be appropriately selected depending on the modification mode. Examples of the binding molecule include specific binding partners (may be added with a labeling substance) to a peptide to which a phosphate group, a DNP group-linked phosphate group or the like is added; labeling substances having a binding site to a thiophosphate group (for example, alkyl halide, maleimide, an aziridine moiety or the like); specific binding partners (may be added with a labeling substance) to various labeling substances; and the like.

The complex containing the modified substrate and the binding molecule may be formed in one stage or in two or more stages. When formed in one stage, for example, the complex can be formed by mixing the modified substrate and the binding molecule. When formed in two stages, for example, after mixing the modified substrate and the binding molecule, the obtained complex and a binding molecule (herein referred to as "binding molecule 2") for the binding molecule (herein referred to as "binding molecule 1") are mixed, whereby a complex further containing the binding molecule 2 in addition to the modified substrate and the binding molecule (binding molecule 1) can be formed.

It is preferred that the complex is formed on a solid phase carrier. This is because, in a later step, recovery of the complex can be performed with a simple operation, and detection of the complex can be performed efficiently. Examples of the solid phase carrier include, but are not particularly limited to, magnetic beads, microplates, and the like. When using magnetic beads as the solid phase carrier, for example, streptavidin-immobilized magnetic beads, biotin-immobilized magnetic beads, or the like can be used as the magnetic beads.

The complex can be formed in a solution. The solution may be a solution suitable for forming a complex. The solution contains a buffer solution such as Tris-HCl buffer solution or HEPES buffer solution; a salt such as sodium chloride; a blocking agent such as bovine serum albumin (BSA); or the like. The pH of the solution may be within the range that maintains functions of the DNP group-containing substrate and the antibody. The pH of the solution is usually 6 to 8, and preferably 6.5 to 7.5.

In the case where the complex is formed in a solution, between the steps (iia) and (iic), it is possible to perform a step of (iib) separating the solid phase carrier on which the complex is formed from the solution. Thereby, contamination of non-specific contaminants, and the like can be suppressed, and detection accuracy of the complex can be improved. For separation of the solid phase carrier and the solution, for example, when using magnetic beads as the solid phase carrier, the solid phase carrier on which the complex is formed and the solution can be separated by collecting the magnetic beads by a magnet. Separation of the solid phase carrier and the solution may be performed by centrifugation or the like. Furthermore, from the viewpoint of suppressing contamination of non-specific contaminants, and the like and improving the detection accuracy of the complex, the solid phase carrier on which the complex has been formed is washed with a washing solution for washing a solid phase carrier.

When the complex contains a labeling substance, the amount of the complex can be measured by detecting the labeling substance in the complex. Specifically, when the labeling substance is a fluorescent substance, fluorescence as a signal is generated by irradiation with excitation light corresponding to the fluorescent substance. By measuring the amount (intensity) of this fluorescence, the amount of the complex can be measured. In this case, using the calibration curve prepared from the known amount of the complex and the amount (intensity) of fluorescence, the amount of the complex is calculated from the measured value of the amount (intensity) of fluorescence. Since the calculated amount of the complex reflects the amount of the modified substrate, the amount can be obtained as the activity value of cyclin-dependent kinase in the test sample.

When the labeling substance is an enzyme, luminescence is generated by acting the enzyme on an enzyme substrate which generates luminescence by a reaction with the enzyme. By detecting the amount (intensity) of this luminescence, the amount of the complex can be measured. In this case, using the calibration curve prepared from the known amount of the complex and the amount (intensity) of luminescence, the amount of the complex is calculated from the measured value of the amount (intensity) of luminescence. Since the calculated amount of the complex reflects the amount of the modified substrate, the amount can be obtained as the activity value of cyclin-dependent kinase in the test sample.

In a preferred embodiment, the substrate of the present disclosure shows specific reactivity to at least one selected from the group consisting of cyclin-dependent kinase 4 and cyclin-dependent kinase 6. For example, showing relatively high reactivity to all cyclin-dependent kinases 1, 2, 4 and 6 is not specific, and it is said as specific that the reactivity to cyclin-dependent kinases 4 and 6 is higher than the reactivity to cyclin-dependent kinase, it is said as specific that the reactivity to cyclin-dependent kinase 4 is higher than the reactivity to cyclin-dependent kinase, and it is said as specific that the reactivity to cyclin-dependent kinase 6 is higher than the reactivity to cyclin-dependent kinase.

Therefore, in a preferred embodiment, the measurement method of the present disclosure is particularly useful as a method for measuring the activity of at least one selected from the group consisting of cyclin-dependent kinase 4 and cyclin-dependent kinase 6, or a method for measuring the activity of cyclin-dependent kinase 6.

3. Reagent and Kit for Measuring Cyclin-Dependent Kinase Activity

The present disclosure, in an embodiment thereof, relates to a reagent for measuring cyclin-dependent kinase activity (sometimes also referred to herein as "the reagent of the present disclosure") containing the substrate of the present disclosure, and a kit for measuring cyclin-dependent kinase activity (sometimes also referred to herein as "the kit of the present disclosure") containing the substrate of the present disclosure. This will be described below.

The reagent of the present disclosure may consist of the substrate of the present disclosure or may contain other components. Examples of the other components include bases, carriers, solvents, dispersants, emulsifiers, buffers, stabilizers, excipients, binders, disintegrators, lubricants, thickeners, humectants, coloring agents, fragrances, chelating agents, and the like.

The content of the substrate of the present disclosure in the reagent of the present disclosure is not particularly limited, and may be, for example, 0.0001 to 100% by mass.

The kit of the present disclosure may consist of only the substrate of the present disclosure or the reagent of the present disclosure, or may contain, as necessary, instruments, reagents, and the like that can be used for performing the measurement method of the present disclosure, in addition.

Examples of the instrument include test tubes, microtiter plates, agarose particles, latex particles, purification columns, epoxy coated slide glass, gold colloid coated slide glass, and the like. In the kit of the present disclosure, the substrate of the present disclosure may be immobilized on a microtiter plate.

Examples of the reagent include antibodies against a peptide to which ATP, an ATP labeled substance, an ATP derivative, a buffer solution, a phosphate group, a DNP group-linked phosphate group or the like is added, substances having a binding site to a thiophosphate group (for example, fluorescent substances, biotin, enzymes, and the like), antibodies against various substances (for example, fluorescent substances, biotin, enzymes, and the like), luminescence detection reagents of various enzymes, positive control samples having cyclin-dependent kinase activity, negative control without having cyclin-dependent kinase activity, and the like.

In a preferred embodiment, the substrate of the present disclosure shows specific reactivity to at least one selected from the group consisting of cyclin-dependent kinase 4 and cyclin-dependent kinase 6. For example, showing relatively high reactivity to all cyclin-dependent kinases 1, 2, 4 and 6 is not specific, and it is said as specific that the reactivity to cyclin-dependent kinases 4 and 6 is higher than the reactivity to cyclin-dependent kinase, it is said as specific that the reactivity to cyclin-dependent kinase 4 is higher than the reactivity to cyclin-dependent kinase, and it is said as specific that the reactivity to cyclin-dependent kinase 6 is higher than the reactivity to cyclin-dependent kinase.

Therefore, in a preferred embodiment, the reagent of the present disclosure and the kit of the present disclosure are particularly useful as a reagent and kit for measuring the activity of at least one selected from the group consisting of cyclin-dependent kinase 4 and cyclin-dependent kinase 6, or as a reagent and kit for measuring the activity of cyclin-dependent kinase 6.

EXAMPLES

Hereinafter, the present invention will be described in detail based on examples, but the present invention is not limited to these examples.

Unless otherwise specified, the solvent of various solutions is water. The constant temperature shaker used for incubation of the reaction solution and washing is SHAKING INCUBATOR SI-300 manufactured by AS ONE Corporation. The amino acid sequence is indicated by one-letter code.

The meaning of each abbreviation is as follows. CDK: cyclin-dependent kinase, BSA: bovine serum albumin, HEPES: 4-(2-hydroxyethyl)-1-piperazine ethanesulfonic acid, NaOH: sodium hydroxide, ATP-γS: adenosine-5'-(γ-thio)-triphosphate, FITC: fluorescein isothiocyanate, EDTA: ethylenediaminetetraacetic acid, DTT: dithiothreitol, St-Av:

streptavidin, TBS-T: Tris buffered saline with Tween 20 (registered trademark), ALP: alkaline phosphatase, HRP: horseradish peroxidase.

Production Example 1. Preparation of Polypeptide 1

A partial peptide of Rb protein which is an in vivo substrate of CDK (Comparative Polypeptide 1), a polypeptide showing higher reactivity than Comparative Polypeptide 1 to CDK4 and CDK6 (Comparative Polypeptide 2), and Polypeptide 1 were synthesized by entrusting to GenScript. The amino acid sequences of these polypeptides are shown in Table 1. These polypeptides were those in which the N-terminal amino acid residues were biotin-modified via a linker (aminohexane).

TABLE 1

| Peptide name | Amino acid sequence (N terminus → C terminus) | SEQ ID NO: |
|---|---|---|
| Polypeptide 1 | GMPWSPNPWWRGGGG | 1 |
| Comparative Polypeptide 1 | PYKISEGLPTPTKMTPRSRI | 2 |
| Comparative Polypeptide 2 | RRRFRPASPLRGPPK | 3 |

Test Example 1. CDK Reactivity Test 1

The reactivity of the polypeptide obtained in Production Example 1 to CDK1, CDK2, CDK4 and CDK6 was examined. Specifically, it was performed as follows.

In a tube, 15 µL of a CDK solution (composition: 10 µg/mL CDK/cyclin complex, 1% BSA, triethanolamine buffer solution (pH 7.5)) containing CDK1/cyclin A2, CDK2/cyclin E1, CDK4/cyclin D3 or CDK6/cyclin D3 (all manufactured by SignalChem) and 15 µL of a kinase reaction solution (composition: 4 µg/mL substrate peptide, 50 mM HEPES-NaOH buffer solution (pH 7.4), 15 mM MgCl$_2$, 2 mM ATP-γS) containing Polypeptide 1, Comparative Polypeptide 1 or Comparative Polypeptide 2 as a substrate peptide were mixed, and the tube was incubated at 37° C. for 1 hour with stirring at 900 rpm using a constant temperature shaker. 21.4 µL of a fluorescent labeling reagent (composition: 180 µg/ml 5-(iodoacetamide)-FITC, 50 mM EDTA, 300 mM MOPS-NaOH, pH 7.4) was added to the tube and pipetted 5 times, then the tube was shielded from light and incubated at 37° C. for 10 minutes with stirring at 400 rpm using a constant temperature shaker. 100 µL of a fluorescent labeling reaction stop solution (composition: 30 mM N-acetyl-L-cysteine, 2 M MOPS-NaOH, pH 7.4) was added to the tube and pipetted 5 times. 30 µL (containing 0.15 µg of magnetic St-Ab beads) of a HISCL HBsAg R2 reagent (manufactured by Sysmex Corporation) was added to the tube, then the tube was shielded from light and incubated at 37° C. for about 10 minutes with stirring at 1600 rpm using a constant temperature shaker. The beads in the tube were precipitated using a magnet, and the supernatant was removed. Then, TBS-T was added, and the beads were washed at 37° C. for about 10 seconds with stirring at 1600 rpm. This washing step was performed three times in total. 100 µL of an ALP-labeled anti-FITC antibody solution (composition: 0.2 to 1 µg/mL ALP-labeled anti-FITC antibody (manufactured by Jackson ImmunoResearch Laboratories, Inc.), 100 mM MES, 150 mM NaCl, 1% BSA, pH 6.5) was added to the tube, then the tube was shielded from light and incubated at 37° C. for about 10 minutes with stirring at 1600 rpm using a constant temperature shaker. The beads in the tube were precipitated using a magnet, and the supernatant was removed. Then, TBS-T was added, and the beads were washed at 37° C. for about 10 seconds with stirring at 1600 rpm. This washing step was performed three times in total. 50 µL of a buffer solution containing Tris (manufactured by Sysmex Corporation, HISCL R4 reagent) was added to the tube and stirred at 2000 rpm at 37° C. for 10 seconds using a constant temperature shaker. 100 µL of a buffer solution (manufactured by Sysmex Corporation, HISCL R5 reagent) containing an ALP luminescent substrate (disodium 2-chloro-5-(4-methoxyspiro{1,2-dioxetane-3,2'-(5'-chloro)-tricyclo[3.3.1.1$^{3,7}$]decan}-4-yl)-1-phenyl phosphate) was added to the tube, then the tube was shielded from light and incubated at 37° C. for 4 minutes with stirring at 1600 rpm using a constant temperature shaker. The beads in the tube were precipitated using a magnet, and the supernatant was transferred to a black plate. Luminescence was detected with a luminometer, and the luminescence intensity was measured.

Figure 2:
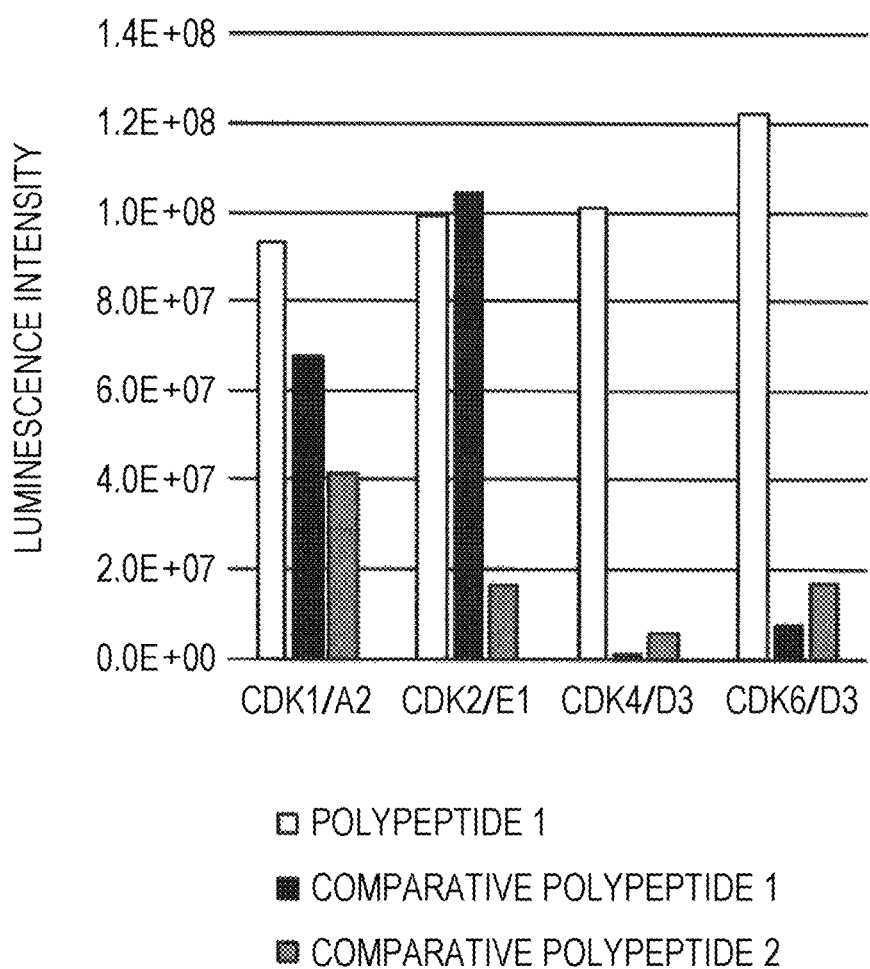
FIG. 2 shows the results of a CDK reactivity test of Test Example 1, the vertical axis is the luminescence intensity representing the reactivity of each polypeptide to CDK, and the horizontal axis shows a complex of CDK and cyclin subjected to measurement of the reactivity.

The measurement results of the luminescence intensity are shown in FIG. 2 and Table 2.

TABLE 2

| Peptide name | Luminescence intensity | | | |
|---|---|---|---|---|
| | CDK1/A2 | CDK2/E1 | CDK4/D3 | CDK6/D3 |
| Polypeptide 1 | 93,190,919 | 99,167,362 | 101,127,359 | 122,281,045 |
| Comparative Polypeptide 1 | 67,564,327 | 104,410,578 | 810,674 | 7,417,238 |
| Comparative Polypeptide 2 | 41,516,306 | 16,211,368 | 5,439,800 | 17,316,904 |

The relative values of the luminescence intensity are shown in Table 3.

TABLE 3

| Peptide name | CDK1/A2 | CDK2/E1 | CDK4/D3 | CDK6/D3 |
|---|---|---|---|---|
| Polypeptide 1 | 2.24 | 6.12 | 18.59 | 7.06 |
| Comparative Polypeptide 1 | 1.63 | 6.44 | 0.15 | 0.43 |
| Comparative Polypeptide 2 | 1.00 | 1.00 | 1.00 | 1.00 |

As shown in FIG. 2, Tables 2 and 3, it was found that the reactivity of Polypeptide 1 to CDK4 was about 18 times higher than the reactivity of Comparative Polypeptide 2, and the reactivity of Polypeptide 1 to CDK6 was about 7 times higher than the reactivity of Comparative Polypeptide 2.

Production Example 2. Preparation of Polypeptide 2

To investigate amino acids important for the reactivity of Polypeptide 1 to CDK4 and CDK6, mutants (Polypeptides 2 to 13) in which each amino acid residue of Polypeptide 1 was mutated to another amino acid residue were synthesized by entrusting to Eurofins Genomics K.K. The amino acid sequences of these polypeptides and Polypeptide 1 are shown in Table 4 (in Table 4, the amino acid residues with bold underline indicate amino acid residues mutated from Polypeptide 1). These polypeptides were those in which the N-terminal amino acid residues were biotin-modified via a linker (aminohexane).

TABLE 4

| Peptide name | Amino acid sequence (N terminus → C terminus) | SEQ ID NO: |
|---|---|---|
| Polypeptide 2 | AMPWSPNPWWRGGGG | 4 |
| Polypeptide 3 | GAPWSPNPWWRGGGG | 5 |
| Polypeptide 4 | GMAWSPNPWWRGGGG | 6 |
| Polypeptide 5 | GMPASPNPWWRGGGG | 7 |
| Polypeptide 6 | GMPWSANPWWRGGGG | 8 |
| Polypeptide 7 | GMPWSPAPWWRGGGG | 9 |
| Polypeptide 8 | GMPWSPNAWWRGGGG | 10 |
| Polypeptide 9 | GMPWSPNPAWRGGGG | 11 |
| Polypeptide 10 | GMPWSPNPWARGGGG | 12 |
| Polypeptide 11 | GMPWSPNPWWAGGGG | 13 |
| Polypeptide 12 | GMPWSPNPWWRAGGG | 14 |
| Polypeptide 13 | GMPFSPNPWWRGGGG | 15 |
| Polypeptide 14 | GMPYSPNPWWRGGGG | 16 |
| Polypeptide 15 | GMPWSWNPWWRGGGG | 17 |
| Polypeptide 16 | GMPWSFNPWWRGGGG | 18 |
| Polypeptide 17 | GMPWSYNPWWRGGGG | 19 |
| Polypeptide A | GMPWSPNPWWHGGGG | 36 |
| Polypeptide B | GMPWSPNPWWKGGGG | 37 |
| Polypeptide C | GMWWSPNPWWRGGGG | 38 |
| Polypeptide D | GMFWSPNPWWRGGGG | 39 |
| Polypeptide E | GMYWSPNPWWRGGGG | 40 |
| Polypeptide F | AMPWSPAPAARAGGG | 41 |
| Polypeptide 1 | GMPWSPNPWWRGGGG | 1 |

Test Example 2. CDK Reactivity Test 2

Test Example 2 was carried out in the same manner as in Test Example 1 except that CDK4 or CDK6 was used as CDK and the polypeptides (Polypeptides 2 to 13) obtained in Production Example 2 or Comparative Polypeptide 2 was used as a substrate peptide. V1 to V4 below:
 V 1: luminescence intensity when using Comparative Polypeptide 2 and CDK4,
 V 2: luminescence intensity when using any of Polypeptides 2 to 17 and A to E, and CDK4,
 V 3: luminescence intensity when using Comparative Polypeptide 2 and CDK6, and
 V 4: luminescence intensity when using any of Polypeptides 2 to 17 and A to E, and CDK6
were measured, and CDK4/6 reactivity was calculated based on the formula ([(V2/V1)+(V4/V3)]/2). CDK4/6 reactivity is a relative value when the CDK4/6 reactivity of Comparative Polypeptide 2 is set as 1. The results are shown in Table 5 (in Table 5, the amino acid residues with bold underline indicate amino acid residues mutated from Polypeptide 1). In Table 5, the same average values calculated based on the results of Test Example 1 are also shown.

TABLE 5

| Peptide name | Amino acid sequence (N terminus → C terminus) | CDK4/6 Reactivity |
|---|---|---|
| Polypeptide 2 | AMPWSPNPWWRGGGG (SEQ ID NO: 4) | 15 |
| Polypeptide 3 | GAPWSPNPWWRGGGG (SEQ ID NO: 5) | 33 |
| Polypeptide 4 | GMAWSPNPWWRGGGG (SEQ ID NO: 6) | 5 |
| Polypeptide 5 | GMPASPNPWWRGGGG (SEQ ID NO: 7) | 1 |
| Polypeptide 6 | GMPWSANPWWRGGGG (SEQ ID NO: 8) | 1 |
| Polypeptide 7 | GMPWSPAPWWRGGGG (SEQ ID NO: 9) | 8 |
| Polypeptide 8 | GMPWSPNAWWRGGGG (SEQ ID NO: 10) | 7 |
| Polypeptide 9 | GMPWSPNPAWRGGGG (SEQ ID NO: 11) | 7 |
| Polypeptide 10 | GMPWSPNPWARGGGG (SEQ ID NO: 12) | 15 |
| Polypeptide 11 | GMPWSPNPWWAGGGG (SEQ ID NO: 13) | 3 |
| Polypeptide 12 | GMPWSPNPWWRAGGG (SEQ ID NO: 14) | 6 |
| Polypeptide 13 | GMPFSPNPWWRGGGG (SEQ ID NO: 15) | 5 |
| Polypeptide 14 | GMPYSPNPWWRGGGG (SEQ ID NO: 16) | 5 |
| Polypeptide 15 | GMPWSWNPWWRGGGG (SEQ ID NO: 17) | 2 |
| Polypeptide 16 | GMPWSFNPWWRGGGG (SEQ ID NO: 18) | 2 |
| Polypeptide 17 | GMPWSYNPWWRGGGG (SEQ ID NO: 19) | 2 |

TABLE 5-continued

| Peptide name | Amino acid sequence (N terminus → C terminus) | CDK4/6 Reactivity |
|---|---|---|
| Polypeptide A | GMPWSPNPWWHGGGG (SEQ ID NO: 36) | 7 |
| Polypeptide B | GMPWSPNPWWKGGGG (SEQ ID NO: 37) | 5 |
| Polypeptide C | GMWWSPNPWWRGGGG (SEQ ID NO: 38) | 5 |
| Polypeptide D | GMFWSPNPWWRGGGG (SEQ ID NO: 39) | 5 |
| Polypeptide E | GMYWSPNPWWRGGGG (SEQ ID NO: 40) | 6 |
| Polypeptide F | AMPWSPAPAARAGGG (SEQ ID NO: 41) | 7 |
| Polypeptide 1 | GMPWSPNPWWRGGGG (SEQ ID NO: 1) | 13 |

From the comparison result between Polypeptide 1 and Polypeptides 6, 15, 16 and 17, when the proline residue of the phosphorylation site sequence (SP) was replaced with an alanine residue, a tryptophan residue, a phenylalanine residue or a tyrosine residue, the CDK4/6 reactivity of Polypeptide 1, which was 13 times the CDK4/6 reactivity of Comparative Polypeptide 2, was reduced to 1 time the CDK4/6 reactivity of Comparative Polypeptide 2. From this, it was found that the proline residue of the phosphorylation site sequence (SP) is important for high reactivity to CDK4 and CDK6.

From the comparison result between Polypeptide 1 and Polypeptides 5, 13, and 14, when the second amino acid residue counting from the proline residue toward the N-terminal side of the phosphorylation site sequence (SP) of Polypeptide 1 was replaced with an alanine residue, the CDK4/6 reactivity of Polypeptide 1, which was 13 times the CDK4/6 reactivity of Comparative Polypeptide 2, was reduced to 1 time the CDK4/6 reactivity of Comparative Polypeptide 2. On the other hand, even when replaced with a phenylalanine residue or a tyrosine residue, it was only reduced to 5 times the CDK4/6 reactivity of Comparative Polypeptide 2. From this, it was found to be important for high reactivity to CDK4 and CDK6 that the second amino acid residue counting from the proline residue toward the N-terminal side of the phosphorylation site sequence (SP) is an aromatic amino acid residue. It was found that, among the aromatic amino acid residues, a tryptophan residue is preferable as the second amino acid residue counting from the proline residue toward the N-terminal side of the phosphorylation site sequence (SP).

From the comparison result between Polypeptide 1 and Polypeptide 11 and Polypeptides A to B, when the fifth amino acid residue counting from the proline residue toward the C-terminal side of the phosphorylation site sequence (SP) of Polypeptide 1 was replaced with an alanine residue, the CDK4/6 reactivity of Polypeptide 1, which was 13 times the CDK4/6 reactivity of Comparative Polypeptide 2, was reduced to 3 times the CDK4/6 reactivity of Comparative Polypeptide 2. On the other hand, even when replaced with H or K, it was only reduced to 5 to 7 times the CDK4/6 reactivity of Comparative Polypeptide 2. Based on the above, from the viewpoint of further improving CDK4/6 reactivity to CDK4 and CDK6, it was found to be preferable that the fifth amino acid residue counting from the proline residue toward the C-terminal side of the phosphorylation site sequence (SP) is a basic amino acid residue. It was found that, among the basic amino acid residues, an arginine residue is more preferable as the fifth amino acid residue counting from the proline residue toward the C-terminal side of the phosphorylation site sequence (SP).

From the comparison result between Polypeptide 1 and Polypeptide 4, when the third amino acid residue counting from the proline residue toward the N-terminal side of the phosphorylation site sequence (SP) of Polypeptide 1 was replaced with an alanine residue, the CDK4/6 reactivity of Polypeptide 1, which was 13 times the CDK4/6 reactivity of Comparative Polypeptide 2, was reduced to 5 times the CDK4/6 reactivity of Comparative Polypeptide 2. From the comparison result between Polypeptide 4 and Polypeptides C to E, in the case where the third amino acid residue counting from the proline residue toward the N-terminal side of the phosphorylation site sequence (SP) of Polypeptide 1 was replaced with an alanine residue, the case where it was replaced with a tryptophan residue, the case where it was replaced with a phenylalanine residue and the case where it was replaced with a tyrosine residue, CDK4/6 reactivity was reduced to the same degree. Based on the above, from the viewpoint of further improving reactivity to CDK4 and CDK6, it was found to be preferable that the third amino acid residue counting from the proline residue toward the N-terminal side of the phosphorylation site sequence (SP) is a proline residue.

From the comparison result between Polypeptide 1 and Polypeptide 12, when the sixth amino acid residue counting from the proline residue toward the C-terminal side of the phosphorylation site sequence (SP) of Polypeptide 1 was replaced with an alanine residue, the CDK4/6 reactivity of Polypeptide 1, which was 13 times the CDK4/6 reactivity of Comparative Polypeptide 2, was reduced to 6 times the CDK4/6 reactivity of Comparative Polypeptide 2. Based on the above, from the viewpoint of further improving reactivity to CDK4 and CDK6, it was found to be preferable that the sixth amino acid residue counting from the proline residue toward the C-terminal side of the phosphorylation site sequence (SP) is a glycine residue.

From the comparison result between Polypeptide 1 and Polypeptide 3, when the fourth amino acid residue counting from the proline residue toward the N-terminal side of the phosphorylation site sequence (SP) of Polypeptide 1 was replaced with an alanine residue, the CDK4/6 reactivity of Polypeptide 1, which was 13 times the CDK4/6 reactivity of Comparative Polypeptide 2, was improved to 33 times the CDK4/6 reactivity of Comparative Polypeptide 2. Based on the above, from the viewpoint of further improving reactivity to CDK4 and CDK6, it was found to be preferable that the fourth amino acid residue counting from the proline residue toward the N-terminal side of the phosphorylation site sequence (SP) is an alanine residue.

From the comparison result between Polypeptide 1 and Polypeptide 8, when the second amino acid residue counting from the proline residue toward the C-terminal side of the phosphorylation site sequence (SP) of Polypeptide 1 was replaced with an alanine residue, the CDK4/6 reactivity of Polypeptide 1, which was 13 times the CDK4/6 reactivity of Comparative Polypeptide 2, was reduced to 7 times the CDK4/6 reactivity of Comparative Polypeptide 2. Based on the above, from the viewpoint of further improving reactivity to CDK4 and CDK6, it was found to be preferable that the second amino acid residue counting from the proline residue toward the C-terminal side of the phosphorylation site sequence (SP) is a proline residue.

From the comparison result between Polypeptide 1 and Polypeptide 9, when the third amino acid residue counting from the proline residue toward the C-terminal side of the phosphorylation site sequence (SP) of Polypeptide 1 was replaced with an alanine residue, the CDK4/6 reactivity of Polypeptide 1, which was 13 times the CDK4/6 reactivity of Comparative Polypeptide 2, was reduced to 7 times the CDK4/6 reactivity of Comparative Polypeptide 2. Based on the above, from the viewpoint of further improving reactivity to CDK4 and CDK6, it was found to be preferable that the third amino acid residue counting from the proline residue toward the C-terminal side of the phosphorylation site sequence (SP) is a tryptophan residue.

From the comparison result between Polypeptide 1 and Polypeptide 7, when the first amino acid residue counting from the proline residue toward the C-terminal side of the phosphorylation site sequence (SP) of Polypeptide 1 was replaced with an alanine residue, the CDK4/6 reactivity of Polypeptide 1, which was 13 times the CDK4/6 reactivity of Comparative Polypeptide 2, was reduced to 8 times the CDK4/6 reactivity of Comparative Polypeptide 2. Based on the above, from the viewpoint of further improving reactivity to CDK4 and CDK6, it was found to be preferable that the first amino acid residue counting from the proline residue toward the C-terminal side of the phosphorylation site sequence (SP) is an asparagine residue.

Production Example 3. Preparation of Polypeptide 3

A polypeptide known as a substrate of CDK4 and CDK6 (Comparative Polypeptide 2), a polypeptide at a portion including a CDK4 phosphorylation site and a CDK6 phosphorylation site in Rb protein which is an in vivo substrate of CDK (Comparative Polypeptide 3) and a polypeptide obtained by replacing the amino acid residue of the CDK4 phosphorylation site with an alanine residue in Comparative Polypeptide 3 (Comparative Polypeptide 4) were synthesized by GenScript synthesis service. The amino acid sequences of these polypeptides are shown in Table 6. These polypeptides were those in which the N-terminal amino acid residues were biotin-modified via a linker (aminohexane). In Comparative Polypeptides 3 and 4, the carboxyl group of the C-terminal amino acid residue is amidated (that is, terminal —COOH becomes —CO—NH$_2$).

TABLE 6

| Peptide name | Amino acid sequence (N terminus → C terminus) | SEQ ID NO: |
| --- | --- | --- |
| Comparative Polypeptide 2 | RRRFRPASPLRGPPK | 3 |
| Comparative Polypeptide 3 | PYKISEGLPTPTKMTPRSRI | 20 |
| Comparative Polypeptide 4 | PYKISEGLPTPAKMAPRSRI | 21 |

Test Example 3. CDK Reactivity Test 3

The reactivity of the polypeptides obtained in Production Example 3 to CDK1, CDK2, CDK4 and CDK6 was examined. Specifically, it was performed as follows.

In a well of a hydrophilic filter plate, 30 μL of a CDK solution (composition: 10 μg/mL CDK/cyclin complex, 1% BSA, triethanolamine buffer solution (pH 7.5)) containing CDK1/cyclin A2, CDK2/cyclin E1, CDK4/cyclin D3 or CDK6/cyclin D3 (all manufactured by SignalChem) and 30 μL of a kinase reaction solution (composition: 4 μg/mL substrate peptide, 50 mM HEPES-NaOH buffer solution (pH 7.4), 15 mM MgCl$_2$, 2 mM ATP-γS) containing any of Comparative Polypeptides 2 to 4 as a substrate peptide were mixed, and the plate was incubated at 37° C. for 1 hour with stirring at 900 rpm using a constant temperature shaker. The reaction solution was recovered by centrifugation (4° C., 2000 rpm, 5 minutes), and 28.6 μL of the reaction solution was dispensed into each well of a PCR plate. 21.4 μL of a fluorescent labeling reagent (composition: 180 μg/ml 5-(iodoacetamide)-FITC, 50 mM EDTA, 300 mM MOPS-NaOH, pH 7.4) was added to the well and pipetted 5 times, then the plate was shielded from light and incubated at 37° C. for 10 minutes with stirring at 400 rpm using a constant temperature shaker. 100 μL of a fluorescent labeling reaction stop solution (composition: 30 mM N-acetyl-L-cysteine, 2 M MOPS-NaOH, pH 7.4) was added to the well and pipetted 5 times. 30 μL (containing 0.15 μg of magnetic St-Ab beads) of a HISCL HBsAg R2 reagent (manufactured by Sysmex Corporation) was added to the well, then the plate was shielded from light and incubated at 37° C. for about 10 minutes with stirring at 1600 rpm using a constant temperature shaker. The beads in the well were precipitated using a magnet, and the supernatant was removed. Then, 180 μL of a HISCL washing solution (manufactured by Sysmex Corporation) was added, and the beads were washed at 37° C. for about 10 seconds with stirring at 1600 rpm. This washing step was performed three times in total. 100 μL of a diluent (4 μg/mL HRP-labeled anti-FITC antibody) by a solution (composition: 100 mM MES, 150 mM NaCl, 1% BSA, pH 6.5) for diluting a HRP-labeled anti-FITC antibody (manufactured by Acris Antibodies GmbH) was added to the well, then the plate was shielded from light and incubated at 37° C. for about 10 minutes with stirring at 1600 rpm using a constant temperature shaker. The beads in the well were precipitated using a magnet, and the supernatant was removed. Then, a HISCL washing solution (manufactured by Sysmex Corporation) was added, and the beads were washed at 37° C. for about 10 seconds with stirring at 1600 rpm. This washing step was performed three times in total. 150 μL of an ELISA Femto reagent (manufactured by Thermo Fisher Scientific Inc.) was added to the well, then the plate was shielded from light and incubated at 37° C. for 4 minutes with stirring at 1600 rpm using a constant temperature shaker. The beads in the well were precipitated using a magnet, then the supernatant was transferred to a black plate. Luminescence was detected with a luminescence plate reader, and the luminescence intensity was measured. For each polypeptide, the relative value of the luminescence intensity when using other CDKs, in the case where the luminescence intensity when using CDK6 was set as 100%, was calculated. The results are shown in Table 7.

TABLE 7

| Peptide name | CDK1/A2 | CDK2/E1 | CDK4/D3 |
|---|---|---|---|
| Comparative Polypeptide 2 | 606% | 198% | 51% |
| Comparative Polypeptide 3 | 678% | 766% | 7% |
| Comparative Polypeptide 4 | 3248% | 2675% | Not detected |

As shown in Table 7, none of Comparative Polypeptides 2 to 4 had specificity to CDK4 or CDK6.

Production Example 4. Preparation of Polypeptide 4

A polypeptide known as a substrate of CDK4 and CDK6 (Comparative Polypeptide 2), other comparative polypeptides (Comparative Polypeptides 5 to 7) and polypeptides obtained by replacing two amino acid residues from the proline residue toward the C-terminal side at the phosphorylation site (SP or TP) of these comparative polypeptides with acidic amino acid residues (Polypeptides 18 to 26) were synthesized by Eurofins Genomics K.K. synthesis service. The amino acid sequences of these polypeptides are shown in Table 8 (in Table 8, the amino acid residues with bold underline indicate amino acid residues mutated from the corresponding comparative polypeptides, and X indicates γ-carboxyglutamic acid). These polypeptides were those in which the N-terminal amino acid residues were biotin-modified via a linker (aminohexane).

TABLE 8

| Peptide name | Amino acid sequence (N terminus → C terminus) | SEQ ID NO: |
|---|---|---|
| Comparative Polypeptide 2 | RRRFRPASPLRGPPK | 3 |
| Polypeptide 18 | RRRFRPASPLDGPPD | 22 |
| Polypeptide 19 | RRRFRPASPLXGPPD | 23 |
| Polypeptide 20 | RRRFRPASPLDGPDK | 24 |
| Polypeptide 21 | RRRFRPASPLEGPPE | 25 |
| Comparative Polypeptide 5 | GGGKAPLTPKKAK | 26 |
| Polypeptide 22 | GGGKAPLTPKDAD | 27 |
| Polypeptide 23 | GGGKAPLTPLDAD | 28 |
| Comparative Polypeptide 6 | GGGRAAPLSPIPHIPR | 29 |
| Polypeptide 24 | GGGRAAPLSPDPHIPD | 30 |
| Polypeptide 25 | GGGRAAPLSPIDHIPD | 31 |
| Comparative Polypeptide 7 | LVEMTGLSPRVIRVW | 32 |
| Polypeptide 26 | LVEMTGLSPRDIRVD | 33 |

Test Example 4. CDK Reactivity Test 4

The reactivity of the polypeptides obtained in Production Example 4 to CDK1, CDK2, CDK4 and CDK6 was examined. Specifically, it was performed as follows.

In a well of a PCR plate, 15 µL of a CDK solution (composition: 10 µg/mL CDK/cyclin complex, 1% BSA, triethanolamine buffer solution (pH 7.5)) containing CDK1/cyclin A2, CDK2/cyclin E1, CDK4/cyclin D3 or CDK6/cyclin D3 (all manufactured by SignalChem) and 15 µL of a kinase reaction solution (composition: 4 µg/mL substrate peptide, 50 mM HEPES-NaOH buffer solution (pH 7.4), 15 mM MgCl$_2$, 2 mM ATP-γS) containing any of Comparative Polypeptides 5 to 7 and Polypeptides 18 to 26 as a substrate peptide were mixed, and the plate was incubated at 37° C. for 1 hour with stirring at 900 rpm using a constant temperature shaker. 21 µL of a fluorescent labeling reagent (composition: 180 µg/ml 5-(iodoacetamide)-FITC, 50 mM EDTA, 300 mM MOPS-NaOH, pH 7.4) was added to the well and pipetted 5 times, then the plate was shielded from light and incubated at 37° C. for 10 minutes with stirring at 400 rpm using a constant temperature shaker. 100 µL of a fluorescent labeling reaction stop solution (composition: 30 mM N-acetyl-L-cysteine, 2 M MOPS-NaOH, pH 7.4) was added to the well and pipetted 5 times. 30 µL (containing 0.15 µg of magnetic St-Ab beads) of a HISCL HBsAg R2 reagent (manufactured by Sysmex Corporation) was added to the well, then the plate was shielded from light and incubated at 37° C. for about 10 minutes with stirring at 1600 rpm using a constant temperature shaker. The beads in the well were precipitated using a magnet, and the supernatant was removed. Then, 180 µL of a HISCL washing solution (manufactured by Sysmex Corporation) was added, and the beads were washed at 37° C. for about 10 seconds with stirring at 1600 rpm. This washing step was performed three times in total. 100 µL of a diluent (1 µg/mL ALP-labeled anti-FITC antibody) by a solution (composition: 100 mM MES, 150 mM NaCl, 1% BSA, pH 6.5) for diluting an ALP-labeled anti-FITC antibody (manufactured by Jackson Immuno Research Laboratories, Inc.) was added to the well, then the plate was shielded from light and incubated at 37° C. for about 10 minutes with stirring at 1600 rpm using a constant temperature shaker. The beads in the well were precipitated using a magnet, and the supernatant was removed. Then, a HISCL washing solution (manufactured by Sysmex Corporation) was added, and the beads were washed at 37° C. for about 10 seconds with stirring at 1600 rpm. This washing step was performed three times in total. 50 µL of a buffer solution containing Tris (manufactured by Sysmex Corporation, HISCL R4 reagent) was added to the well, and the plate was stirred at 2000 rpm at 37° C. for 10 seconds using a constant temperature shaker. 100 µL of a buffer solution (manufactured by Sysmex Corporation, HISCL R5 reagent) containing an ALP luminescent substrate (disodium 2-chloro-5-(4-methoxyspiro{1,2-dioxetane-3,2'-(5'-chloro)-tricyclo[3.3.1.1$^{3,7}$]decan}-4-yl)-1-phenyl phosphate) was added to the well, then the plate was shielded from light and incubated at 37° C. for 4 minutes with stirring at 1600 rpm using a constant temperature shaker. The beads in the well were precipitated using a magnet, then 100 µL of the supernatant was transferred to a black plate. Luminescence was detected with a luminescence plate reader, and the luminescence intensity was measured. For each polypeptide, the relative value of the luminescence intensity when using other CDKs, in the case where the luminescence intensity when using CDK6 was set as 100%, was calculated. The results are shown in Table 9 (in Table 9, the amino acid residues with bold underline indicate amino acid residues mutated from the corresponding comparative polypeptides, and X indicates γ-carboxyglutamic acid).

TABLE 9

| Peptide name | Amino acid sequence (N terminus → C terminus) | CDK1/A2 | CDK2/E1 | CDK4/D3 |
|---|---|---|---|---|
| Comparative Polypeptide 2 | RRRFRPASPLRGPPK (SEQ ID NO: 3) | 318% | 321% | 245% |
| Polypeptide 18 | RRRFRPASPLDGPPD (SEQ ID NO: 22) | 22% | Not detected | 14% |
| Polypeptide 19 | RRRFRPASPLXGPPD (SEQ ID NO: 23) | Not detected | Not detected | Not detected |
| Polypeptide 20 | RRRFRPASPLDGPDK (SEQ ID NO: 24) | Not detected | Not detected | Not detected |
| Polypeptide 21 | RRRFRPASPLEGPPE (SEQ ID NO: 25) | Not detected | Not detected | Not detected |
| Comparative Polypeptide 5 | GGGKAPLTPKKAK (SEQ ID NO: 26) | 143% | 156% | 56% |
| Polypeptide 22 | GGGKAPLTPKDAD (SEQ ID NO: 27) | 27% | 15% | 46% |
| Polypeptide 23 | GGGKAPLTPLDAD (SEQ ID NO: 28) | Not detected | Not detected | 37% |
| Comparative Polypeptide 6 | GGGRAAPLSPIPHIPR (SEQ ID NO: 29) | 119% | 44% | 190% |
| Polypeptide 24 | GGGRAAPLSPDPHIPD (SEQ ID NO: 30) | Not detected | 54% | 54% |
| Polypeptide 25 | GGGRAAPLSPIDHIPD (SEQ ID NO: 31) | Not detected | 62% | 40% |
| Comparative Polypeptide 7 | LVEMTGLSPRVIRVW (SEQ ID NO: 32) | 1146% | 10% | 55% |
| Polypeptide 26 | LVEMTGLSPRDIRVD (SEQ ID NO: 33) | 295% | Not detected | 18% |

As shown in Table 9, it was found to be important for specificity to CDK4 and CDK6, particularly CDK6 that at least two amino acid residues from the proline residue toward the C-terminal side of the phosphorylation site (SP or TP) were acidic amino acid residues.

Production Example 5. Preparation of Polypeptide 5

Polypeptides (Polypeptides 27 and 28) obtained by introducing a mutation (mutation of at least two amino acid residues from the proline residue toward the C-terminal side of the phosphorylation site (SP or TP) to acidic amino acid residues) that is important for the specificity to CDK4 and CDK6, particularly the specificity to CDK6, which was revealed in Test Example 4, into the polypeptide (Polypeptide 3) which was found to have high reactivity to CDK4 and CDK6 in Test Example 2 were synthesized by entrusting to Eurofins Genomics K.K. The amino acid sequences of these polypeptides are shown in Table 10 (in Table 10, the amino acid residues with bold underline indicate amino acid residues mutated from Polypeptide 3). These polypeptides were those in which the N-terminal amino acid residues were biotin-modified via a linker (aminohexane).

TABLE 10

| Peptide name | Amino acid sequence (N terminus → C terminus) | SEQ ID NO: |
|---|---|---|
| Polypeptide 3 | GAPWSPNPWWRGGGG | 5 |
| Polypeptide 27 | GAPWSPNDWWDGGGG | 34 |
| Polypeptide 28 | GAPWSPDPWDDGGGG | 35 |

Test Example 5. CDK Reactivity Test 5

The reactivity of the polypeptides obtained in Production Example 5 to CDK1, CDK2, CDK4 and CDK6 was examined in the same manner as in Test Example 4. The reactivity to each CDK was calculated as a relative value with the reactivity when using Polypeptide 3 is set as 100%. The results are shown in Table 11.

TABLE 11

| Peptide name | Amino acid sequence (N terminus → C terminus) | CDK1/A2 | CDK2/E1 | CDK4/D3 | CDK6/D3 |
|---|---|---|---|---|---|
| Polypeptide 3 | GAPWSPNPWWRGGGG (SEQ ID NO: 5) | 100% | 100% | 100% | 100% |
| Polypeptide 27 | GAPWSPNDWWDGGGG (SEQ ID NO: 34) | 13% | 20% | 37% | 33% |
| Polypeptide 28 | GAPWSPDPWDDGGGG (SEQ ID NO: 35) | 4% | 13% | 50% | 25% |

As shown in Table 11, it was found that, by introducing a mutation important to the specificity to CDK4 and CDK6, particularly the specificity to CDK6, which was revealed in Test Example 4, into Polypeptide 3, the reactivity to CDK1 and CDK2 is further reduced, and the specificity to CDK4 and CDK6 is consequently improved.

Test Example 6. CDK Reactivity Test 6

The reactivity of the polypeptide (Polypeptide 28) obtained in Production Example 5 to CDK1, CDK2, CDK4 and CDK6 was examined using an automated immunoassay system (manufactured by Sysmex Corporation, HISCL-800). Specifically, it was performed as follows.

In a well of a plate, 30 µL of a CDK solution (composition: 0.01 to 10 µg/mL CDK/cyclin complex, 1% BSA, triethanolamine buffer solution (pH 7.5)) containing CDK1/cyclin A2, CDK2/cyclin E1, CDK4/cyclin D3 or CDK6/cyclin D3 (all manufactured by SignalChem) and 30 µL of a kinase reaction solution (composition: 4 µg/mL substrate peptide, 50 mM HEPES-NaOH buffer solution (pH 7.4), 15 mM $MgCl_2$, 16 mM ATP) containing Polypeptide 28 as a substrate peptide were mixed, and the plate was incubated at 42° C. for 3 minutes. 30 µL (containing 0.15 µg of magnetic St-Ab beads) of a HISCL HBsAg R2 reagent (manufactured by Sysmex Corporation) was added to the well, and the plate was incubated at 42° C. for 2 minutes. The beads in the well were precipitated using a magnet, and the supernatant was removed. Then, a HISCL washing solution (manufactured by Sysmex Corporation) was added, and the beads were washed by shaking several times. 100 µL of a detection antibody solution (composition: 0.1 µg/mL polyclonal anti-phospho-antibody (manufactured by Abcam plc.), 0.3 µg/mL ALP-labeled polyclonal anti-rabbit antibody (manufactured by Dako), 100 mM MES, 150 mM NaCl, 1% BSA, pH 6.5) was added to the well, and the plate was incubated at 42° C. for 3 minutes. The beads in the tube were precipitated using a magnet, and the supernatant was removed. Then, a HISCL washing solution (manufactured by Sysmex Corporation) was added, and the beads were washed by shaking several times. 50 µL of a buffer solution containing Tris (manufactured by Sysmex Corporation, HISCL R4 reagent) was added to the well, and the plate was stirred. 100 µL of a buffer solution (manufactured by Sysmex Corporation, HISCL R5 reagent) containing an ALP luminescent substrate (disodium 2-chloro-5-(4-methoxyspiro{1,2-dioxetane-3,2'-(5'-chloro)-tricyclo[$3.3.1.1^{3,7}$]decan}-4-yl)-1-phenyl phosphate) was added to the well, then the plate was incubated at 42° C. for 5 minutes. Luminescence was detected with a luminometer, and the luminescence intensity was measured. The results are shown in FIG. 3.

Figure 3:
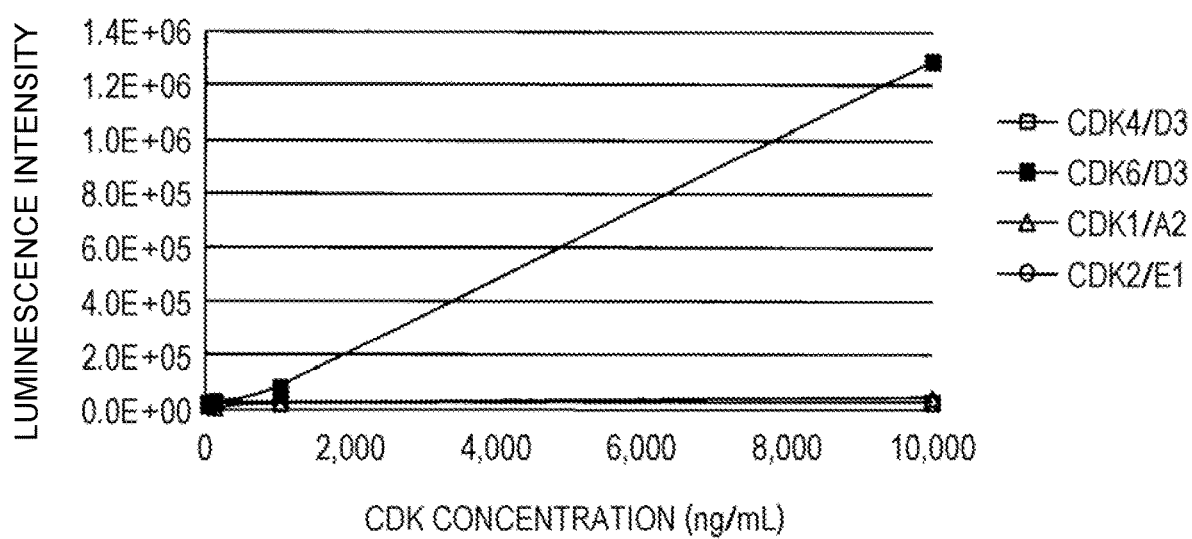
FIG. 3 shows the results of a CDK reactivity test of Test Example 6, the vertical axis is the luminescence intensity representing the reactivity to each CDK, and the horizontal axis shows CDK concentration at the time of reactivity measurement.

As shown in FIG. 3, it was found that, in this test system, Polypeptide 28 is a substrate capable of specifically detecting CDK6.

What is claimed is:

1. A method for measuring the cyclin-dependent kinase activity of a test sample, the method comprising steps (i) and (ii):
   (i) bringing the test sample into contact with a cyclin-dependent kinase substrate; and
   (ii) measuring the amount of a substance produced by cyclin-dependent kinase in the test sample, wherein the substrate comprises a polypeptide that contains an amino acid sequence represented by formula (1): $R^1$—P wherein $R^1$ represents a serine residue or a threonine residue, P represents a proline residue, "—" represents a single bond, and the left side represents the N-terminal side, and satisfies (a1) and/or (b1):
   (a1) the second amino acid residue counting from the proline residue toward the N-terminal side in the formula (1) is an aromatic amino acid residue, and/or
   (b1) at least two amino acid residues from the proline residue toward the C-terminal side in the formula (1) are acidic amino acid residues,
   wherein the substance produced in step (ii) is a modified substrate, and
   wherein the measuring of step (ii) comprises steps (iia)-(iic):
   (iia) mixing the modified substrate with a binding molecule for the modified substrate, to form a complex containing the modified substrate and the binding molecule, wherein the complex is formed within a solution on a solid phase carrier;
   (iib) separating the solid phase carrier on which the complex is formed from the solution; and
   (iic) measuring the amount of the modified substrate by measuring the amount of the complex.

2. The method according to claim 1, wherein the substrate satisfies (a2):
   (a2) the fifth amino acid residue counting from the proline residue toward the C-terminal side in the formula (1) is a basic amino acid.

3. The method according to claim 1, wherein the substrate satisfies (a3):
   (a3) the third amino acid residue counting from the proline residue toward the N-terminal side in the formula (1) is a ring structure-containing amino acid residue.

4. A method for measuring the cyclin-dependent kinase activity of a test sample, the method comprising steps (i) and (ii):
   (i) bringing the test sample into contact with a cyclin-dependent kinase substrate; and
   (ii) measuring the amount of a substance produced by cyclin-dependent kinase in the test sample, wherein the substrate comprises a polypeptide that contains an amino acid sequence represented by formula (1): R1—P wherein R1 represents a serine residue or a threonine residue, P represents a proline residue, "—" represents a single bond, and the left side represents the N-terminal side, and satisfies (a1) and (b1):

(a1) the second amino acid residue counting from the proline residue toward the N-terminal side in the formula (1) is an aromatic amino acid residue, and (b1) at least two amino acid residues from the proline residue toward the C-terminal side in the formula (1) are acidic amino acid residues, wherein the substance produced in step (ii) is a modified substrate, and wherein the measuring of step (ii) comprises steps (iia)-(iic):

(iia) mixing the modified substrate with a binding molecule for the modified substrate, to form a complex containing the modified substrate and the binding molecule, wherein the complex is formed within a solution on a solid phase carrier;

(iib) separating the solid phase carrier on which the complex is formed from the solution; and (iic) measuring the amount of the modified substrate by measuring the amount of the complex.

5. The method according to claim 1, wherein the substrate satisfies (b3):

(b3) at least two amino acid residues of the first to tenth amino acid residues counting from the proline residue toward the C-terminal side in the formula (1) are acidic amino acid residues.

* * * * *

SEQUENCE LISTING

```
<160> NUMBER OF SEQ ID NOS: 41

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide, polypeptide 1

<400> SEQUENCE: 1

Gly Met Pro Trp Ser Pro Asn Pro Trp Trp Arg Gly Gly Gly Gly
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide, comparative polypeptide 1

<400> SEQUENCE: 2

Pro Tyr Lys Ile Ser Glu Gly Leu Pro Thr Pro Thr Lys Met Thr Pro
1               5                   10                  15
```

Arg Ser Arg Ile
            20

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide, comparative polypeptide 2

<400> SEQUENCE: 3

Arg Arg Arg Phe Arg Pro Ala Ser Pro Leu Arg Gly Pro Pro Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide, polypeptide 2

<400> SEQUENCE: 4

Ala Met Pro Trp Ser Pro Asn Pro Trp Trp Arg Gly Gly Gly Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide, polypeptide 3

<400> SEQUENCE: 5

Gly Ala Pro Trp Ser Pro Asn Pro Trp Trp Arg Gly Gly Gly Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide, polypeptide 4

<400> SEQUENCE: 6

Gly Met Ala Trp Ser Pro Asn Pro Trp Trp Arg Gly Gly Gly Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide, polypeptide 5

<400> SEQUENCE: 7

Gly Met Pro Ala Ser Pro Asn Pro Trp Trp Arg Gly Gly Gly Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide, polypeptide 6

<400> SEQUENCE: 8

Gly Met Pro Trp Ser Ala Asn Pro Trp Trp Arg Gly Gly Gly Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide, polypeptide 7

<400> SEQUENCE: 9

Gly Met Pro Trp Ser Pro Ala Pro Trp Trp Arg Gly Gly Gly Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide, polypeptide 8

<400> SEQUENCE: 10

Gly Met Pro Trp Ser Pro Asn Ala Trp Trp Arg Gly Gly Gly Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide, polypeptide 9

<400> SEQUENCE: 11

Gly Met Pro Trp Ser Pro Asn Pro Ala Trp Arg Gly Gly Gly Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide, polypeptide 10

<400> SEQUENCE: 12

Gly Met Pro Trp Ser Pro Asn Pro Trp Ala Arg Gly Gly Gly Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide, polypeptide 11

<400> SEQUENCE: 13

Gly Met Pro Trp Ser Pro Asn Pro Trp Trp Ala Gly Gly Gly Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide, polypeptide 12

<400> SEQUENCE: 14

Gly Met Pro Trp Ser Pro Asn Pro Trp Trp Arg Ala Gly Gly Gly

```
<210> SEQ ID NO 15
<211> LENGTH: 15
<212> TYPE: PRT
<213> ORGANISM: Artificial Sequence
<220> FEATURE:
<223> OTHER INFORMATION: Synthetic peptide, polypeptide 13

<400> SEQUENCE: 15

Gly Met Pro Phe Ser Pro Asn Pro Trp Trp Arg Gly Gly Gly Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide, polypeptide 14

<400> SEQUENCE: 16

Gly Met Pro Tyr Ser Pro Asn Pro Trp Trp Arg Gly Gly Gly Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide, polypeptide 15

<400> SEQUENCE: 17

Gly Met Pro Trp Ser Trp Asn Pro Trp Trp Arg Gly Gly Gly Gly
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide, polypeptide 16

<400> SEQUENCE: 18

Gly Met Pro Trp Ser Phe Asn Pro Trp Trp Arg Gly Gly Gly Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide, polypeptide 17

<400> SEQUENCE: 19

Gly Met Pro Trp Ser Tyr Asn Pro Trp Trp Arg Gly Gly Gly Gly
1               5                   10                  15

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide, comparative polypeptide 3

<400> SEQUENCE: 20

Pro Tyr Lys Ile Ser Glu Gly Leu Pro Thr Pro Thr Lys Met Thr Pro
1               5                   10                  15
```

Arg Ser Arg Ile
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide, comparative polypeptide 4

<400> SEQUENCE: 21

Pro Tyr Lys Ile Ser Glu Gly Leu Pro Thr Pro Ala Lys Met Ala Pro
1               5                   10                  15

Arg Ser Arg Ile
            20

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide, polypeptide 18

<400> SEQUENCE: 22

Arg Arg Arg Phe Arg Pro Ala Ser Pro Leu Asp Gly Pro Pro Asp
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide, polypeptide 19
<220> FEATURE:
<221> NAME/KEY: misc_feature
<222> LOCATION: (11)..(11)
<223> OTHER INFORMATION: Xaa can be any naturally occurring amino acid

<400> SEQUENCE: 23

Arg Arg Arg Phe Arg Pro Ala Ser Pro Leu Xaa Gly Pro Pro Asp
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide, polypeptide 20

<400> SEQUENCE: 24

Arg Arg Arg Phe Arg Pro Ala Ser Pro Leu Asp Gly Pro Asp Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide, polypeptide 21

<400> SEQUENCE: 25

Arg Arg Arg Phe Arg Pro Ala Ser Pro Leu Glu Gly Pro Pro Glu
1               5                   10                  15

<210> SEQ ID NO 26
<211> LENGTH: 13

```
<212> TYPE: PRT
<213> ORGANISM: Artificial Sequence
<220> FEATURE:
<223> OTHER INFORMATION: Synthetic peptide, comparative polypeptide 5

<400> SEQUENCE: 26

Gly Gly Gly Lys Ala Pro Leu Thr Pro Lys Lys Ala Lys
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic peptide, polypeptide 22

<400> SEQUENCE: 27

Gly Gly Gly Lys Ala Pro Leu Thr Pro Lys Asp Ala Asp
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic peptide, polypeptide 23

<400> SEQUENCE: 28

Gly Gly Gly Lys Ala Pro Leu Thr Pro Leu Asp Ala Asp
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Synthetic peptide, comparative polypeptide 6

<400> SEQUENCE: 29

Gly Gly Gly Arg Ala Ala Pro Leu Ser Pro Ile Pro His Ile Pro Arg
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic peptide, polypeptide 24

<400> SEQUENCE: 30

Gly Gly Gly Arg Ala Ala Pro Leu Ser Pro Asp Pro His Ile Pro Asp
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic peptide, polypeptide 25

<400> SEQUENCE: 31

Gly Gly Gly Arg Ala Ala Pro Leu Ser Pro Ile Asp His Ile Pro Asp
1               5                   10                  15

<210> SEQ ID NO 32
<211> LENGTH: 15
<212> TYPE: PRT
```

```
<213> ORGANISM: Artificial Sequence
<220> FEATURE:
<223> OTHER INFORMATION: Synthetic peptide, comparative polypeptide 7

<400> SEQUENCE: 32

Leu Val Glu Met Thr Gly Leu Ser Pro Arg Val Ile Arg Val Trp
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide, polypeptide 26

<400> SEQUENCE: 33

Leu Val Glu Met Thr Gly Leu Ser Pro Arg Asp Ile Arg Val Asp
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic peptide, polypeptide 27

<400> SEQUENCE: 34

Gly Ala Pro Trp Ser Pro Asn Asp Trp Trp Asp Gly Gly Gly Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic peptide, polypeptide 28

<400> SEQUENCE: 35

Gly Ala Pro Trp Ser Pro Asp Pro Trp Asp Asp Gly Gly Gly Gly
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic peptide, polypeptide A

<400> SEQUENCE: 36

Gly Met Pro Trp Ser Pro Asn Pro Trp Trp His Gly Gly Gly Gly
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic peptide, polypeptide B

<400> SEQUENCE: 37

Gly Met Pro Trp Ser Pro Asn Pro Trp Trp Lys Gly Gly Gly Gly
1               5                   10                  15

<210> SEQ ID NO 38
<211> LENGTH: 15
<212> TYPE: PRT
<213> ORGANISM: Artificial Sequence
```

```
<220> FEATURE:
<223> OTHER INFORMATION: Synthetic peptide, polypeptide C

<400> SEQUENCE: 38

Gly Met Trp Trp Ser Pro Asn Pro Trp Trp Arg Gly Gly Gly Gly
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide, polypeptide D

<400> SEQUENCE: 39

Gly Met Phe Trp Ser Pro Asn Pro Trp Trp Arg Gly Gly Gly Gly
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide, polypeptide E

<400> SEQUENCE: 40

Gly Met Tyr Trp Ser Pro Asn Pro Trp Trp Arg Gly Gly Gly Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide, polypeptide F

<400> SEQUENCE: 41

Ala Met Pro Trp Ser Pro Ala Pro Ala Ala Arg Ala Gly Gly Gly
1               5                   10                  15
```